US00PP07846P

United States Patent [19]

Stravers

[11] Patent Number: Plant 7,846

[45] Date of Patent: Mar. 31, 1992

[54] GERBERA PLANT NAMED TERMOGAT

[75] Inventor: Lambertus J. M. Stravers, Kudelstaart, Netherlands

[73] Assignee: Terra Nigra BV, PA De Kwakel, Netherlands

[21] Appl. No.: 606,845

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner

[57] ABSTRACT

A new and distinct cultivar of Gerbera plant named Termogat, characterized by its orange outer ray floret color, relatively large bright red inner florets, and its green disc.

1 Drawing Sheet

1

The present invention comprises a new and distinct cultivar of Gerbera plant, botanically known as *Gerbera jamesonii,* and referred to by the cultivar name Termogat.

Termogat was originated from a hybridization made in a controlled breeding program in De Kwakel, The Netherlands in 1985 under the supervision of the inventor Lambertus J. M. Stravers.

The female parent was 83.175. The male parent was 82.103. The new cultivar was discovered and selected as one flowering plant within the progeny of the stated parentage by the inventor on or about January 1986 in a controlled environment in De Kwakel.

The first asexual reproduction of Termogat was accomplished when vegetative cuttings were taken from the initial selection in April 1986 in a controlled environment in De Kwakel, The Netherlands by a technician working under formulations established and supervised by the inventor. The new cultivar is presently being propagated by cuttings and tissue culture. Horticultural examination of selected units initiated in November 1986 has demonstrated that the combination of characteristics as herein disclosed for Termogat are firmly fixed and are retained through successive generations of asexual reproduction.

Termogat has not been observed under all possible environmental conditions. The phenotype may vary significantly with variations in environment such as temperature, light intensity and day length. The following observations, measurements and comparisons describe plants grown in the greenhouse of Terra Nigra BV in De Kwakel, The Netherlands under controlled conditions which closely approximate those generally used in commercial practice.

The following traits have been repeatedly observed and have been determined to be basic characteristics of Termogat, which in combination provide a new and distinct cultivar:

1. Semi-double flowers, generally funnel shape in form.
2. Orange ray florets, and bright red inner or double florets.
3. A center disc which is green when mature and immature.
4. The inner florets are large in diameter relative to the total flower diameter, thereby providing a unique color combination of orange, red and green.

Of the many commercial cultivars known to the present inventor, there is no cultivar sufficiently similar to

2

Termogat so as to provide a meaningful basis for comparison.

The accompanying photographic drawing shows typical inflorescence characteristics of Termogat, with the colors being as nearly true as possible with illustrations of this type. The leaves of Termogat are described below but are not illustrated. The photograph comprises a closeup view of the novel flower form and color.

In the following description, color references are made to The Royal Horticultural Society Colour Chart (RHS). The color values were determined approximately mid day on Dec. 11, 1989 under artificial light at De Kwakel, The Netherlands.

Classification:

*Botanical.*—*Gerbera jamesonii* cv. Termogat.

*Commercial.*—Gerbera.

Parentage: Seedling from cross of cultivars designated 83.175 and 82.103.

Plant: The plant when fully grown reaches a height of 40 cm.

Leaf Blade:

*Length.*—Medium.

*Width.*—Medium.

*Thickness.*—Medium.

*Blistering (puckering).*—Medium.

*Hairiness on upper side.*—Absent.

*Depth of cuts or incisions in leaf.*—Near bottom or base: Deep. Near middle: Deep. Near tip: Shallow.

*Color.*—Upper surface of leaf, dark green; lower surface, light green.

*Glossiness on upper side.*—Medium.

*Angle at tip.*—Reflexed.

*Shape at tip.*—Pointed.

*Margin of lobes.*—Sinuate.

*Petiole length.*—Medium.

*Petiole anthocyanin coloration.*—Present, medium in intensity.

Peduncle:

*Length.*—Medium.

*Cross section.*—Round, medium strength and thickness.

*Resistance to bending.*—Medium.

*Hairiness.*—Medium.

*Color.*—Medium green.

*Anthocyanin.*—Present at base, medium in intensity, none present at tip.

*Bracts near tip.*—None.

Flower head:

*Type.*—Semi-double; generally funnel shaped in form.

*Diameter from edge to edge.*—Medium; 11-12 cm. in diameter.

*Height.*—Distance from top of attachment of involucre to top of flower head is medium.

*Involucre.*—Height: Medium. Diameter: Medium. Number of bracts: Medium; longitudinal axis on inner rows are reflexing. Anthocyanin: Absent. Hairiness: Medium.

*Outer row ray florets.*—Number in outer row: Medium. Length of floret: Medium. Width of floret: Medium. Shape of floret: Narrow, elliptic; longitudinal folding medium. Shape of tip: Rounded, one tooth, shallow in depth. Axis (longitudinal) of florets: Reflexing. Cross section of floret: Convex. Length of free petals: Short. Color distribution on inner side: Lighter towards base.

Striation: Present. Claw spot: Absent. Color on top side: 25B. Color on bottom side: Between 47B and 23C.

*Inner florets.*—Diameter: Large. Color: Bright red. Longitudinal axis: Straight.

*Disc florets.*—Diameter: Medium. Main color of perianth lobes: Red for both male and female flowers. Color (mature and immature): Green.

Reproductive parts:

*Stigma.*—Main color, yellow.

*Anthers.*—Main color, dark yellow; color at top lighter relative to other parts; longitudinal stripes are absent.

*Pappus.*—Main Color: Yellow; uniform color throughout. Orientation: Level of top is above closed disc florets.

I claim:

1. A new and distinct cultivar of Gerbera plant named Termogat, as illustrated and described.

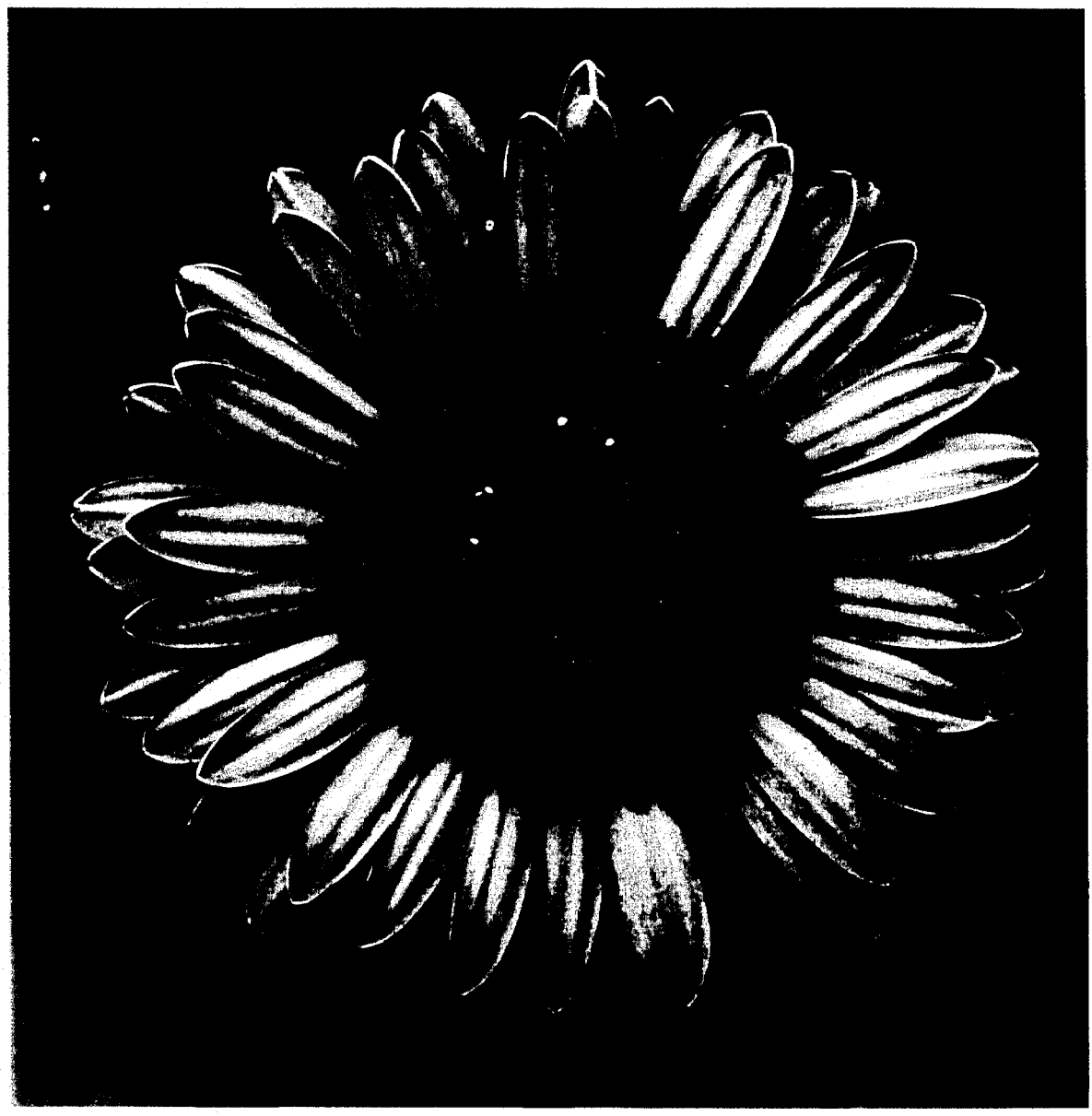

* * * * *